(12) United States Patent
Gudkov

(10) Patent No.: US 8,242,057 B2
(45) Date of Patent: Aug. 14, 2012

(54) METHODS FOR IDENTIFYING MODULATORS OF APOPTOSIS

(75) Inventor: Andrei V. Gudkov, Gates Mills, OH (US)

(73) Assignee: Cleveland Biolabs, Inc., Buffalo, NY (US)

( * ) Notice: Subject to any disclaimer, the term of this patent is extended or adjusted under 35 U.S.C. 154(b) by 843 days.

(21) Appl. No.: 11/768,847

(22) Filed: Jun. 26, 2007

(65) Prior Publication Data

US 2007/0298974 A1    Dec. 27, 2007

Related U.S. Application Data

(60) Provisional application No. 60/805,849, filed on Jun. 26, 2006.

(51) Int. Cl.
*C40B 30/06*    (2006.01)
*C12Q 1/00*    (2006.01)

(52) U.S. Cl. ............................................. 506/10; 435/4

(58) Field of Classification Search ................... 506/10; 435/4
See application file for complete search history.

(56) References Cited

U.S. PATENT DOCUMENTS

| | | | |
|---|---|---|---|
| 6,153,380 A * | 11/2000 | Nolan et al. | 435/6 |
| 6,525,091 B2 | 2/2003 | Robinson | |
| 7,396,651 B2 | 7/2008 | Adler | |
| 7,407,745 B1 | 8/2008 | Sowa | |

OTHER PUBLICATIONS

Albayrak et al., 2003, A high-throughput screen for single gene activities: isolation of apoptosis inducers, Biochemical and Biophysical Research Communications, 304: 772-776.*

Izquierdo et al., 1998, Vault-related resistance to anticancer drugs determined by the expression of the major vault protein LRP, Cytotechnology 27: 137-148.*

* cited by examiner

*Primary Examiner* — Amber D Steele
(74) *Attorney, Agent, or Firm* — Polsinelli Shughart PC; Teddy C. Scott, Jr.; Ron Galant

(57) ABSTRACT

Provided herein is a method for screening a modulator of apoptosis by contacting a cell comprising a FAS mediated apoptosis system, major vault protein and cytochrome b, with a candidate modulator, and measuring the level of apoptosis of the cell. The modulator of apoptosis is identified by a change in apoptosis in comparison to a control.

15 Claims, 7 Drawing Sheets

METHODS FOR IDENTIFYING MODULATORS OF APOPTOSIS

CROSS REFERENCE TO RELATED APPLICATIONS

This application claims the benefit of U.S. Provisional Application No. 60/805,849, filed Jun. 26, 2006, which is incorporated by reference in its entirety.

FIELD OF THE INVENTION

The present invention relates to methods and compositions for identifying modulators of apoptosis.

BACKGROUND

Cancer is the second leading cause of death in the United States today. By the time a solid tumor cancer is clinically detectable, a tumor may be several centimeters in diameter and spread to other organs. Removal of the primary tumor may stimulate tumors to enter a phase of rapid growth and initiate their own vasculature. This rapid growth of secondary tumors may be due to the result of a cancer cell's own resistance to apoptosis.

Apoptotic cell death via the FAS-mediated system provides balanced cell proliferation and renewal with cell turnover. Cancer cells have developed a number of biological mechanisms to avoid apoptosis. For example, lung and colon cancer cells secrete elevated levels of soluble "decoy" molecules that bind to FasL, thereby inhibiting its binding to Fas. A cancer cell can also resist the effects of FAS-mediated apoptosis by expressing one or more of its own intracellular inhibitory molecules that bind to an intermediate protein of FAS-mediated apoptosis.

While potential cancer therapeutic compounds have been identified that modulate FAS-mediated apoptosis, these compounds have proven to not be effective in slowing tumor growth at a fast enough rate for reducing the probability of metastasis. Accordingly, there remains a need for methods which can effectively screen for modulators of apoptosis.

SUMMARY OF THE INVENTION

Provided herein may be a method to screen for modulators of major vault protein. The method may comprise providing a cell that comprises MVP and a FAS-mediated apoptosis system, and contacting the cell with a candidate MVP modulator compound. A modulator of major vault protein is identified by a change in apoptosis as compared to a control. The identified modulator of MVP may also be a modulator of FAS-mediated apoptosis. The method may be performed using high throughput methods and in vitro.

The cells may be mammalian cells, such as Chinese hamster ovary cells (CHO) or HeLa cells, or non-mammalian cells. The cells may express MVP, a FAS-mediated apoptosis protein, or a candidate modulator of MVP from heterologous DNA or from endogenous DNA. The method further provides vectors that may encode MVP, any component of the FAS-mediated apoptosis system, and the MVP modulator candidate. These vectors may be expressed in a host cell of choice ("heterologous expression").

The modulator compound may be a small molecule, peptide, nucleic acid, antibody, polypeptide, drug, or organic compound. The modulator compound may be screened from a library of compounds. A library of compounds may include random peptide libraries, cDNA libraries, oligosaccharide libraries, natural products libraries, phage libraries, small molecule libraries, and combinatorial libraries.

The method also provides use of FAS-mediated apoptosis system proteins. A FAS protein may be encoded by a nucleic acid and variants thereof. The FAS-mediated apoptosis system may be induced by any protein or compound that binds to the FAS receptor. The FAS receptor ligand may be selected from the group consisting of FAS receptor antibodies, FAS-L, FAS receptor specific ligands, and non-specific FAS receptor ligands.

DETAILED DESCRIPTION

Figure 1:
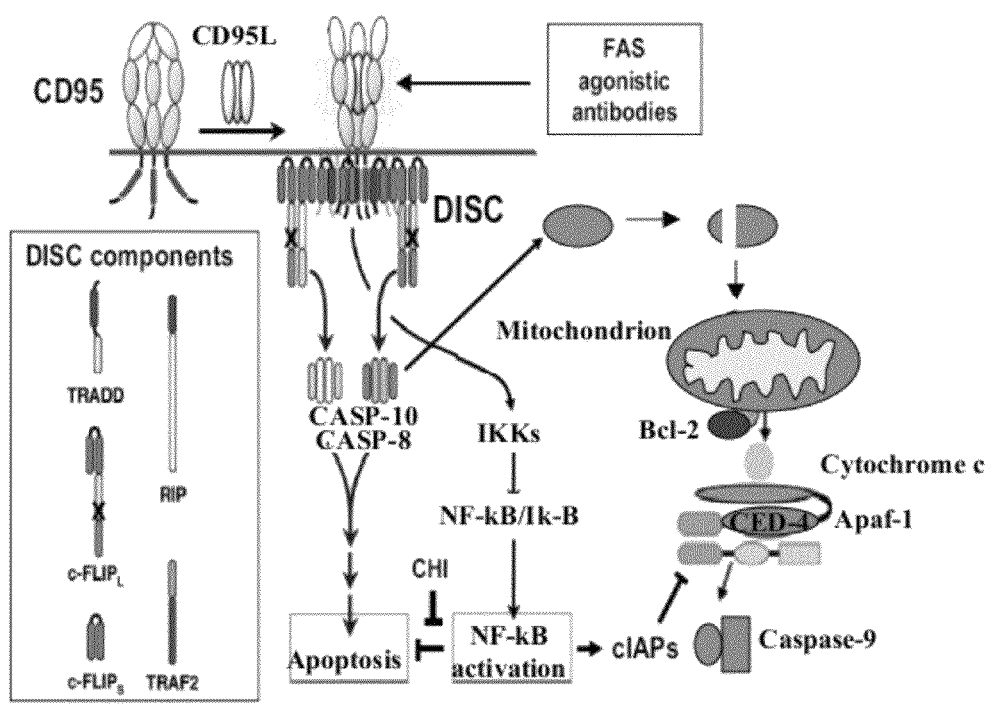
FIG. 1 shows an abridged schematic of the FAS apoptosis system or pathway.

The inventors have made the surprising discovery that cytochrome b is part of the FAS-mediated apoptosis system and that MVP binds to, and inhibits FAS system protein cytoplasmic cytochrome b. Overexpression of MVP may lead to inhibition of cytoplasmic cytochrome b at a level that uncontrolled cell proliferation occurs because less cells are diminished by apoptosis.

Provided herein is a screen for modulators of MVP that are identified by measuring apoptosis of FAS-ligand stimulated cells. These modulators can be identified based upon their ability to enhance, inhibit, or decrease the level of apoptosis in a population of cells. These modulators alone or in combination have a variety of uses, for example, as a component of a therapeutic composition for treating cancer and other apoptosis-related conditions.

1. Definitions

The terminology used herein is for the purpose of describing particular embodiments only and is not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Antibody

"Antibody" as used herein may mean an antibody of classes IgG, IgM, IgA, IgD or IgE, or fragments or derivatives thereof, including Fab, F(ab')2, Fd, and single chain antibodies, diabodies, bi-specific antibodies, bi-functional antibodies and derivatives thereof. The F(ab) and F(ab')$_2$ fragments may be generated by treating an antibody with an enzyme, such as pepsin. Light chains are classified as either kappa or lambda. The antibody may be a monoclonal antibody, polyclonal antibody, affinity-purified antibody, or fragments/mixtures thereof, which exhibit sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety.

b. Apoptosis

"Apoptosis" as used herein may mean cell death. Apoptosis may be a result of stimulating the FAS apoptotic pathway. Apoptosis is may be programmed cell death. Apoptosis may be characterized by cell death or morphological changes as curved cell surface, condensed nuclear chromatin and fragmented chromosomal DNA.

c. Candidate Modulator Compound

"Candidate modulator compound" as used herein may mean any compound wherein the characterization of the compound's ability to modulate is desirable. Exemplary candidate compounds or substrates include small molecules, peptides, nucleic acids, antibodies, polypeptides, drugs, and organic compounds.

d. cDNA Library

"cDNA library" as used herein may mean a library of complementary DNA molecules synthesized from mRNA molecules in a cell.

e. Combinatorial Library

"Combinatorial library" as used herein may mean any library constructed from taking a small number of starting compounds and reacting them with a larger number of reagents.

f. Heterologous Sequence

"Heterologous sequence" or a "heterologous nucleic acid," as used herein may mean one that originates from a source foreign to the particular cell, or, if from the same source, is modified from its original form. Thus, a heterologous gene in a cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

g. Library

"Library" as used herein may mean a collection of different molecules. A variety of different types of libraries can be used with the methods of the present invention. Libraries are intentionally created collections of different molecules which are prepared using organic synthetic methods or biochemically. In the latter case, the molecules can be made in vitro or in vivo. A non-exhaustive list of such libraries includes random peptide libraries, combinatorially synthesized libraries, natural product libraries, oligosaccharide libraries and legacy libraries (a collection of molecules synthesized over time and collected, such as by a group of chemists at a particular research facility for example).

h. Ligand

"Ligand" as used herein may mean an entity which has an intrinsic binding affinity for the target. The ligand can be a molecule, or a portion of a molecule that binds the target. The ligands are may be small organic molecules which have an intrinsic binding affinity for the target molecule, but may also be other sequence-specific binding molecules, such as peptides (D-, L- or a mixture of D- and L-), peptidomimetics, complex carbohydrates or other oligomers of individual units or monomers which bind specifically to the target. The term also includes various derivatives and modifications that are introduced in order to enhance binding to the target. Ligands that inhibit a biological activity of a target molecule are called "inhibitors" of the target.

i. Modulate

"Modulate" as used herein may mean any altering of activity, such as regulate, down regulate, upregulate, reduce, inhibit, increase, decrease, deactivate, or activate.

j. Natural Products Library

"Natural products library" as used herein may mean any library of naturally occurring compounds. An example of a natural products library may be an oligosaccharide library (York et al., Carb. Res., 285:99-128, 1996; Liang et al., Science, 274:1520-1522, 1996; Ding et al., Adv. Expt. Med. Biol., 376:261-269, 1995; each of which is incorporated herein by reference).

k. Nucleic Acid Fragment

"Nucleic acid fragment" as used herein may mean a nucleic acid which may be employed at any length, with the total length being limited by the ease of preparation and use in the intended recombinant DNA protocol. Illustrative nucleic acid segments may be useful with total lengths of about 10,000, about 5000, about 3000, about 2,000, about 1,000, about 500, about 200, about 100, about 50 base pairs in length, and the like.

l. Operably Linked

"Operably linked" as used herein may mean a functional linkage between a nucleic acid expression control sequence (such as a promoter, signal sequence, or array of transcription factor binding sites) and a second polynucleotide, wherein the expression control sequence affects transcription and/or translation of the second polynucleotide.

m. Small Molecules

"Small molecules" as used herein may mean a molecule usually less than about 10 kDa molecular weight. Small molecules may be synthetic organic or inorganic compounds, peptides, (poly)nucleotides, (oligo)saccharides and the like. Small molecules specifically include small non-polymeric (i.e. not peptide or polypeptide) organic and inorganic molecules. Many pharmaceutical companies have extensive libraries of such molecules, which may be inconveniently screened by using the herein described methods. Small molecules may have molecular weights of less than about 1000 Da, about 750 Da, or about 500 Da.

n. Substantially Complementary

"Substantially complementary" as used herein may mean that a first sequence is at least 50%, 55%, 60%, 65%, 70%, 75%, 80%, 85%, 90%, 95%, 96%, 97%, 98%, or 99% identical to the complement of a second sequence over a a region of 8, 9, 10, 20, 30, 40, 50, 60, 70, 80, 90, 100, 150, 200, 250, 300, 350 or more nucleotides or amino acids nucleotides, or amino acids. Intermediate lengths may mean any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. Substantial complementary may also mean that the two nucleotide sequences hybridize under stringent hybridization conditions using the methods described herein, (e.g., BLAST analysis using standard parameters, as described below)

o. Substantially Identical

"Substantially identical" as used herein may mean that a first and second nucleotide or amino acid sequence are at least about 70%, 75%, 80%, 85%, 90%, 91%, 92%, 93%, 94%, 95%, 96%, 97%, 98%, or 99% identical over a region of 8, 9, 10, 20, 30, 40, 50, 60, 70, 80, 90, 100, 150, 200, 250, 300, 350 or more nucleotides or amino acids. Intermediate lengths may mean any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. Substantially identical may also mean the first sequence nucleotide or amino acid sequence is substantially complementary to the complement of the second sequence.

p. Variant

"Variant" as used herein in the context of a nucleic acid may mean a substantially identical or substantially complementary sequence. A variant in reference to a nucleic acid may further mean a nucleic acid that may contain one or more substitutions, additions, deletions, insertions, or may be fragments thereof. A variant may also be a nucleic acid capable of hybridizing under moderately stringent conditions and specifically binding to a nucleic acid encoding the agent. Hybridization techniques are well known in the art and may be conducted under moderately stringent conditions.

A variant in reference to a peptide may further mean differing from a native peptide in one or more substitutions, deletions, additions and/or insertions, or a sequence substantially identical to the native peptide sequence. The ability of a variant to react with antigen-specific antisera may be enhanced or unchanged, relative to the native protein, or may be diminished by less than 50%, or less than 20%, relative to the native peptide. Such variants may generally be identified by modifying one of the peptide sequences encoding an agent and evaluating the reactivity of the modified peptide with antigen-specific antibodies or antisera as described herein. Variants may include those in which one or more portions have been removed such as an N-terminal leader sequence or transmembrane domain. Other variants may include variants in which a small portion (e.g., 1-30 amino acids, or 5-15 amino acids) has been removed from the N- and/or C-terminal of the mature protein.

A variant in reference to a peptide may contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also contain nonconservative changes. Variant peptides differ from a native sequence by substitution, deletion or addition of five amino acids or fewer. Variants may also be modified by deletion or addition of amino acids, which have minimal influence on the immunogenicity, secondary structure and hydropathic nature of the polypeptide.

q. Vector

"Vector" as used herein may mean a nucleic acid molecule capable of transporting another nucleic acid to which it has been linked, such as a plasmid. The vector may be capable of extra-chromosomal replication, such as an episome. The vector may be capable directing expression of the nucleic acid to which it is operatively linked, such as an expression vectors.

2. Method of Identifying Modulators of MVP a. Providing Cells

A method is provided herein for screening and identifying modulators of MVP and other proteins involved in the FAS-mediated apoptosis. The method may comprise providing a host cell that comprises major vault protein and a FAS-mediated apoptosis system as described herein.

b. Contacting Host Cell

The method may comprise contacting the host cell with a candidate modulator compound. The method may comprise stimulating the host cell to express the candidate modulator compound. The method may comprise providing the host cell with FAS ligand to stimulate FAS-mediated apoptosis.

c. Components of the Assay (1) Major Vault Protein

Major vault protein is provided herein that may be used to identify modulators of MVP. MVP may comprise a protein. The MVP may be expressed (in vitro or in vivo) using a nucleic acid described herein. MVP may comprise a polypeptide sequence or a variant thereof or fragment thereof. MVP may be associated with one or more proteins or nucleic acids of the vault complex. This association may be direct or indirect.

MVP may be associated with one or more other vault components. The forces driving direct association between MVP and other vault components may stem from electrostatic (including salt bridges and hydrogen bonds) protein-protein interactions between complementary surfaces. Indirect association may be the result of MVP associating with a second vault component through one or more other components.

MVP may be chemoresistant. MVP expression may be chemoresistant in broad panels of unselected tumor cell lines and untreated clinical cancers of different histogenic origins. MVP overexpression may result in elevated resistance to particular drugs. MVP may be a potential mediator of cytochrome b apoptotic function in the cytoplasm by inhibiting apoptosis through the modulation of cytochrome b function. Modulation of cytochrome b function by MVP may be through sequestering and/or inhibition of cytochrome b function to mediate apoptosis via the FAS-apoptosis pathway.

(2) Vault Complex

In the alternative, the method may be used to identify modulators of vault complex. Vault complex may comprise MVP. Vault complex may comprise a cytoplasmic ribonucleoprotein organelle. Vault complex may comprise a protein and a nucleic acid. Vault complex may comprise a plurality of proteins and ribonucleic acids. Vault complex may comprise major vault protein, vault poly-(ADP-ribose) polymerase, telomerase-associated protein 1, and a nucleic acid. The nucleic acid may be a small untranslated RNA molecule. The small untranslated RNA molecule may be at least 50, 60, 70, 80, 90, 100, 110, 120, 130, 140, 150 nucleotide bases in length. The vault complex may be at least 5, 6, 7, 8, 9, 10, 11, 12, 13, 14, 15, 16, 17, 18, 19, 20, 21, 22, 23, 24, 25, 26, 30, 40, or 50 megadaltons in size. The vault complex may be found in the cytoplasm of a cell. The vault complex may be associated with the nucleus. The vault complex may have a hollow barrel-shaped structure characteristic of proteins involved in intracellular transport. Vault complex may contribute to chemoresistance by transporting and sequestering of drugs.

(3) FAS-Mediated Apoptosis System

The method for screening modulators of MVP may also employ the FAS-mediated apoptosis system. The FAS-mediated system may comprise a protein. The FAS-mediated system may comprise a plurality of proteins. The FAS-mediated system may comprise FAS (APO-1/CD95), FAS-ligand (FAS-L), DISC, caspase 3, caspase 8, caspase 9, caspase 10, BID, BCL-2, cytochrome c, cytochrome b, APAF-1, cFLIP, NF-kB, AP1, NF-AT, or combinations thereof. Members of the FAS-mediated system may be expressed (in vitro or in vivo) using a nucleic acid described herein. The FAS-mediated system may comprise a polypeptide sequence or a variant thereof or fragment thereof. FAS-mediated apoptosis system may support the homeostoasis of the immune system and mediate its protective response against pathogens.

FAS may be a member of the tumor necrosis factor receptor superfamily. FAS may exist in an inactive or active receptor complex on cell surfaces. Interaction between FAS-receptor and FAS-ligand (CD95L) may trigger transformation of these receptor complexes allowing for the formation of a death-inducing signaling complex (DISC). FAS (APO-1/CD95), an important member of the tumor necrosis factor receptor superfamily, may exist as an inactive receptor complex on cell surfaces. FAS receptor interaction with a FAS receptor ligand (CD95L) may trigger transformation of these receptor complexes, allowing for the formation of a death-inducing signaling complex (DISC). This complex may induce a series of downstream apoptotic events, including the transmission of cell death signals to the mitochondria. See FIG. 1. DISC complex formation may lead to the cleavage of caspase 8 and 10. Caspase 8 may be involved in the amplification of apoptotic response through a mitochondrial apoptotic pathway, wherein it cleaves BID (BH3 interacting domain death agonist), which then translocates to the mitochondria. Once at the mitochondria, BID may participate in the release of cytochrome c and cytochrome b into the cytoplasm. Specifically, BID may induce apoptosis by interfering with mitochondrial function by inhibiting Bcl-2. Bcl-2 inhibits apoptotic death, and its overexpression has been implicated in tumors such as B-cell membrane permeability, allowing intramitochondrial proteins to escape into the cytosol. Cytochrome c may active apoptosome, leading to cleavage of caspase 9. Caspase 9 may activate caspase 3, resulting in apoptosis. Caspase 3 in turn activates caspase 8, thereby completing a positive feedback loop.

Figure 2:
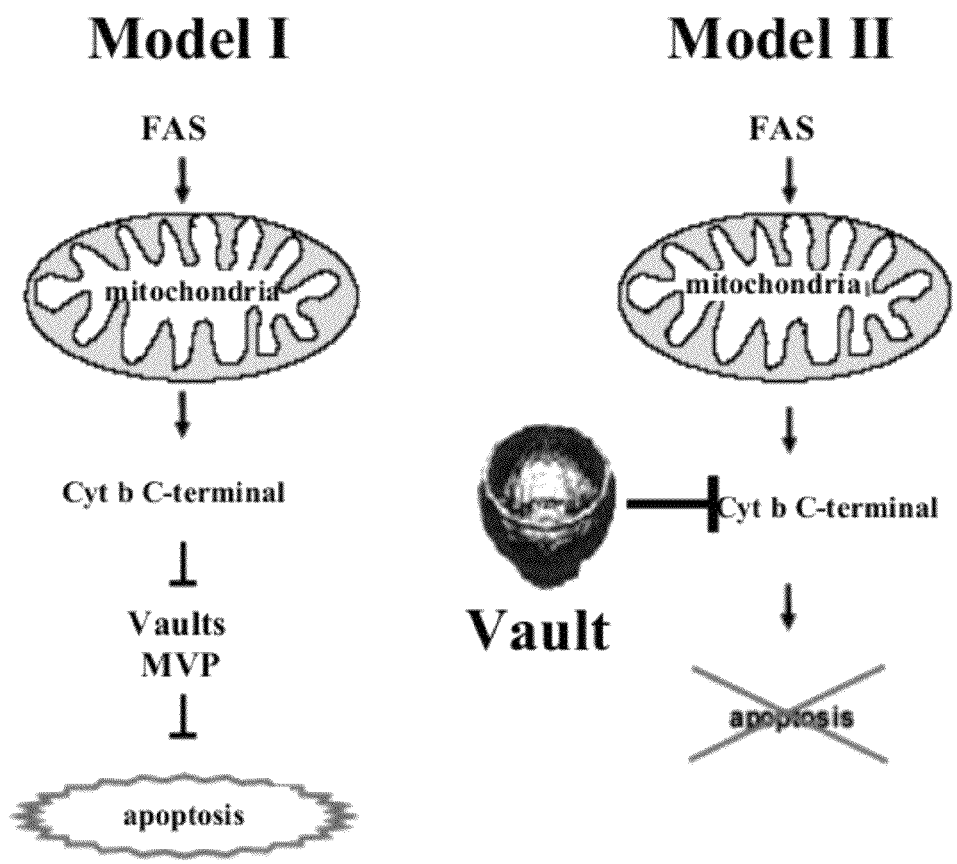
FIG. 2 shows an abridged schematic of MVP inhibiting the FAS apoptosis pathway. Major vault protein may inhibit FAS apoptosis by binding to cytochrome b released from mitochondria.

Initiation of FAS apoptosis may trigger cytochrome b processing in its resident location, the mitochondria. This processing may result in the cleavage and release of the C-terminus of cytochrome b into the cytoplasm. The ectopic expression of cytochrome b in the cytoplasm has been found to exhibit pro-apoptotic effects. MVP may be a natural, endogenous modulator of cytochrome b-dependent apoptosis. See FIG. 2.

Cytochrome b may mediate FAS apoptosis through inactivation of the anti-apoptotic function of the MVP and/or vault complex. Cytochrome b may be inhibited by the action of MVP and/or vault, whereby FAS-mediated apoptosis is inhibited. Cytoplasmic localization of cytochrome b induces apoptosis and contributes to the regulation of FAS-mediated apoptosis. One or more of the FAS-mediated apoptosis system components may be expressed from a heterologous sequence within the cell.

(4) Modulator Compound

The method may also employ a MVP modulator compound to be screened. A modulator of MVP compound may be expressed from an nucleic acid. A variety of different types of libraries of modulator compounds of MVP can be used and screened in the method of the present invention.

A modulator of MVP may be an antibody, a small molecule, a drug, a peptide, a nucleic acid, an oligosaccharide, or an inorganic compound. An identified modulator compound may be derived from a library of candidate modulator compounds. A library of compounds may be a combinatorial library.

(5) Nucleic Acid

Also provided herein is a nucleic acid that encodes MVP or a variant thereof. A nucleic acid may also encode FAS-mediated system or variants thereof. The nucleic acid may also encode a modulator or a candidate modulator compound. The nucleic acid may comprise native sequences such as an endogenous sequence.

The nucleic acid may be combined with other DNA sequences, such as promoters, polyadenylation signals, polyhistidine signals additional restriction enzyme sites, multiple cloning sites, other coding segments, and the like. Nucleic acids may also be capable of hybridizing under moderately stringent conditions and specifically binding to a nucleic of an agent. Hybridization techniques are well known in the art of molecular biology. Suitable moderately stringent conditions for testing the hybridization of a nucleic acid with other nucleic acids may include pre-washing in a solution of 5×SSC, 0.5% SDS, 1.0 mM EDTA (pH 8.0); hybridizing at 50° C., or 65° C., 5×SSC, overnight; followed by washing twice at 65° C. for 20 minutes with each of 2×, 0.5× and 0.2×SSC containing 0.1% SDS.

As a result of the degeneracy of the genetic code, amino acid similarity, reading frame positioning and the like, there are many nucleic acid sequences that may encode MVP or a FAS system component or a candidate modulator of MVP or candidate modulator of MVP. Nucleic acids of MVP or a FAS system component or a candidate modulator of MVP may vary due to differences in codon usage. Further, alleles of the genes comprising the nucleic acid sequences of MVP or a FAS system component or a candidate modulator of MVP are within the scope of the present invention. The resulting mRNA and protein may have an altered structure or function. Alleles may be identified using standard techniques (such as hybridization, amplification and/or database sequence comparison).

The nucleic acid may be used to synthesize or express (in vitro or in vivo) the agent. The nucleic acid may be cloned into a vector for recombinant expression as described below.

(6) Vectors

Also provided herein is a vector that comprises the nucleic acid. The vector may be an expression vector. The vector may comprise a nucleic acid sequence or plurality thereof encoding the amino acid sequences. The vector may express the nucleic acid in a heterologous expression alone or in combination with a cell's endogenous expression of MVP, FAS-mediated apoptosis, and a modulator compound or library thereof.

The expression vector may include one or more control sequences capable of effecting and/or enhancing the expression of the agent. Control sequences that are suitable for expression in prokaryotes, for example, include a promoter sequence, an operator sequence, and a ribosome binding site. Control sequences for expression in eukaryotic cells may include a promoter, an enhancer, and a transcription termination sequence (i.e. a polyadenylation signal).

The expression vector may also include other sequences, such as, for example, nucleic acid sequences encoding a signal sequence or an amplifiable gene. A signal sequence may direct the secretion of a polypeptide fused thereto from a cell expressing the protein. In the expression vector, nucleic acid encoding a signal sequence may be linked to a polypeptide coding sequence so as to preserve the reading frame of the polypeptide coding sequence.

(7) Host Cells

Provided herein is a host cell that comprises a vector. A wide variety of host cells are available for propagation and/or expression of vectors. Examples include, viruses (phage, DNA, RNA), prokaryotic cells, (such as E. coli and strains of Bacillus, Pseudomonas, and other bacteria), yeast or other fungal cells (including S. cerevisiae and P. pastoris), insect cells, plant cells, as well as higher eukaryotic cells (such as HeLa cells, CHO cells, human embryonic kidney cells, and other mammalian cells).

Vectors expressing any member of a peptide or cDNA library, or any other peptide or nucleic acid, may be introduced into a host cell by any convenient method, which will vary depending on the vector-host system employed. Generally, a vector may be introduced into a host cell by transformation or infection (also known as "transfection") with a virus (e.g., phage) bearing the vector. If the host cell is a prokaryotic cell (or other cell having a cell wall), convenient transformation methods may include the calcium treatment method described by Cohen, et al. (1972) Proc. Natl. Acad. Sci., USA 69:2110-14. If a prokaryotic cell is used as the host and the vector is a phagemid vector, the vector may be introduced into the host cell by transfection. Yeast cells may be transformed using polyethylene glycol, for example, as taught by Hinnen (1978) *Proc. Natl. Acad. Sci, USA,* 75:1929-33. Mammalian cells are conveniently transformed using the calcium phosphate precipitation method described by Graham, et al. (1978) *Virology,* 52:546 and by Gorman, et al. (1990) DNA and *Prot. Eng. Tech.,* 2:3-10. However, other known methods for introducing DNA into host cells, such as nuclear injection, electroporation, protoplast fusion, and other means also are acceptable for use in the invention.

Host cell culture conditions may allow transcription, translation, and protein transport between cellular compartments. Factors that affect these processes are well-known and include, for example, DNA/RNA copy number; factors that stabilize DNA; nutrients, supplements, and transcriptional inducers or repressors present in the culture medium; temperature, pH and osmolarity of the culture; and cell density. The adjustment of these factors to promote expression in a particular vector-host cell system is within the level of skill in the art. Principles and practical techniques for maximizing the productivity of in vitro mammalian cell cultures, for example, may be found in Mammalian Cell Biotechnology: a Practical Approach (Butler ed., IRL Press (1991).

Any of a number of well-known techniques for large- or small-scale production of proteins may be employed in expressing the agent. These may include the use of a shaken flask, a fluidized bed bioreactor, a roller bottle culture system, and a stirred tank bioreactor system. Cell culture may be carried out in a batch, fed-batch, or continuous mode.

Methods for recovery of the candidate compound(s) are well-known and vary depending on the expression system employed. A compound including a signal sequence may be recovered from the culture medium or the periplasm. The agent may also be expressed intracellularly and recovered from cell lysates.

The expressed modulator compound, or candidate modulator compound, may be purified from culture medium or a cell lysate by any method capable of separating the compound from one or more components of the host cell or culture medium. The compound may be separated from host cell and/or culture medium components that would interfere with the intended use of the compound. As a first step, the culture medium or cell lysate may be centrifuged or filtered to remove cellular debris. The supernatant may then typically concentrated or diluted to a desired volume or diafiltered into a suitable buffer to condition the preparation for further purification.

The compound may then be further purified using well-known techniques. The technique chosen will vary depending on the properties of the compound. For example, the compound may be purified using an affinity column containing the cognate binding partner of a binding member of the compound. For instance, the agent fused with green fluorescent protein, hemagglutinin, or FLAG epitope tags or with hexa-histidine or similar metal affinity tags may be purified by fractionation on an affinity column.

Compounds identified in the herein described method as modulators of MVP can also be further evaluated, detected, cloned, sequenced, and the like, either in solution or after binding to a solid support. For recovery of an expressed candidate compound, the host cell may be cultured under conditions suitable for cell growth and expression and the expressed compound recovered from a cell lysate or, if the candidate compounds are secreted, from the culture medium. In particular, the culture medium may contain appropriate nutrients and growth factors for the host cell employed. The nutrients and growth factors are, in many cases, well known or may be readily determined empirically by those skilled in the art. Suitable culture conditions for mammalian host cells, for instance, are described in Mammalian Cell Culture (Mather ed., Plenum Press 1984) and in Barnes and Sato (1980) *Cell* 22:649.

(8) Control Cells

The method of screening and identifying modulators of MVP may use control cells in the analysis. Control calls may be contacted by the candidate modulator compound and compared with cells comprising the FAS mediated apoptosis system and MVP. The control cells can be used to aid in the identification of MVP modulators from a pool or library of candidates. For example, a positive control cell for identifying a candidate modulator that inhibits MVP may be a cell that does not express one or more proteins of the FAS apoptosis pathway. Another example of a positive control for identifying a candidate modulator that inhibits MVP may be a cell that inhibits expression of MVP, but not the FAS-mediated apoptosis system. MVP expression may be inhibited by microRNA. A negative control may comprise contacting the candidate modulator compound with a cell that does not express MVP. Other controls may include the use of known MVP inhibitors such as a short hairpin RNA set forth in the below-identified Examples.

(9) FAS Ligand

The method may employ a ligand to initiate signaling in the FAS-mediated apoptosis system. Any ligand that triggers apoptosis via the FAS-mediated apoptosis system may be used. Ligands may include FAS receptor agonistic antibodies, FAS-L, and any other compound, small molecule, antibody, or peptide.

(10) Labels

The method may use a detection label. The detectable label may be a radioactive label (such as, e.g., $^3$H, $^{125}$I, $^{35}$S, $^{14}$C, $^{32}$P, and $^{33}$P), an enzymatic label used for enzyme immunoassay (such as, e.g., horseradish peroxidase, alkaline peroxidase, glucose 6-phosphate dehydrogenase, luciferase and the like), a chemiluminescent label (such as, e.g., acridinium esters, luminal, isoluminol, thioesters, sulfonamides, phenanthridinium esters, and the like), a fluorescence label (such as, e.g., fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

Detectable labels may be measured by radioactive, calorimetric, or fluorescence imaging or other visual means. For example, the detection label can be measured in relative light units by a fluorescent imager.

d. Measuring Level of Apoptosis

The method provided herein screens for modulators of MVP. Candidate modulators of MVP may be determined as modulators of MVP based upon the level of apoptosis of a cell population in comparison with a control. Methods of apoptosis measurement may be employed to identify cells undergoing apoptosis, or identify cells which have undergone apoptosis.

(1) DNA Cleavage

Apoptosis can be identified by the cleavage of DNA at internucleosomal sites in a population of cells. This procedure may involve DNA extraction, processing, separation by size, and a means of quantifying intact and cleaved DNA. By examining individual cells within a population, the morphological appearance of apoptosis can be discerned by decreased cell size with condensed, often fragmented, nuclei.

(2) DNA Labeling

A more sensitive morphological test for apoptosis is the terminal deoxynucleotidyl transferase (Tdt)-linked labeling of DNA ends which gives an extremely intense signal in apoptotic cells as compared to nonapoptotic cells.

Apoptosis may be directly measured by determining the level of incorporation of a labeled nucleoside into genomic DNA. Examples include the tritiated thymidine (3H-dT) and bromodeoxyuridine (BrdU) methods (Waldman et al., 1991, Modern Pathol. 4:718-722; Gratzner, 1982, Science 218:474-475). Other direct measurement methods may include cell counting, optical density readings, and direct observation of cell layer confluency.

Indirect methods have also been used in specific cases. Interest in $CD4^+$ T lymphocyte turnover in AIDS, for example, has been stimulated by indirect estimates of T cell proliferation based on their rate of accumulation in the circulation following initiation of effective anti-retroviral therapy (Ho et al., 1995, Nature 373:123-126; Wei et al., 1995, Nature 373:117-122).

(3) Detection of Apoptosis

Indicators of apoptosis may be used. Suitable apoptosis labels include DAPI. Accordingly, these agents can be used as an affinity ligand, and attached to a solid support such as a bead, a surface, etc. and used to pull out cells that are undergoing apoptosis. Similarly, these agents can be coupled to a fluorescent dye such as PerCP, and then used as the basis of a fluorescent-activated cell sorting (FACS) separation.

(4) Other Ways to Measure Apoptosis

Sensitive assays that measure various biological and morphological hallmarks of the apoptotic process are known in the art. For example, a monoclonal antibody which may be used to detect cleavage of poly (ADP-ribose) polymerase, CCP32/Caspase-3 fluorescent and calorimetric assay kits, and a FLICE/caspase-8 fluorescent assay kit are commercially available (Clontech Laboratories, Inc.). Annexin V apoptosis assays, measuring the translocated phosphatidylserine (PS) are described, e.g., in Dachary-Prigent et al., Blood 81:2554-65 (1993); Thiagarajan and Tait, J. Biol. Chem. 265:17420-3 (1990); and Zhang et al., Biotechniques 23:525-31 (1997). Identification of apoptosis in situ via specific labeling of nuclear DNA fragmentation is described in Gavrieli et al., J. Cell Biol. 119:493-50 (1992).

e. Performing the Assay

The method described herein may be performed using a high throughput method well known in the art, or an in vitro method.

3. Therapeutic Method

A method is provided herein for administering to a subject in need thereof a composition comprising a modulator of MVP. The modulator of MVP may be identified using the screening method as described herein. The subject in need thereof may be suffering from uncontrolled tumor or cell growth. The MVP modulator may enhance or interfere with the activity of MVP. The method may comprise the step of administering a pharmaceutical composition of the MVP modulator. The pharmaceutical composition may be prepared in various forms such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

MVP modulators identified by the herein described method, may be compounds showing pharmacological activity or therapeutical activity. Compounds with pharmacological activity are able to enhance or interfere with the activity of MVP or a fragment thereof. The compounds having the desired pharmacological activity may be administered in a physiologically acceptable carrier to a host, as previously described.

The agents may be administered in a variety of ways, orally, parenterally e.g., subcutaneously, intraperitoneally, intravascularly, etc. Depending upon the manner of introduction, the compounds may be formulated in a variety of ways. The concentration of a therapeutically active compound in the formulation may vary from about 0.1-100 wt %. Modulators of the present invention can be administered at a rate determined by the LD-50 of the modulator, and the side-effects of the modulator at various concentrations, as applied to the mass and overall health of the subject. Administration can be accomplished via single or divided doses.

The identified modulators of the invention may be used alone or in conjunction with other agents that are known to be beneficial in treating or preventing human diseases that are mediated by MVP. The modulators of the invention and another agent may be co-administered, either in concomitant therapy or in a fixed combination, or they may be administered at separate times.

4. Assay Kits

The invention also provides test kits for assaying for modulators of MVP. Test kits according to the invention include one or more reagents such as a candidate modulator for practicing the assay according to the invention.

EXAMPLES

Example 1

Novel Component of FAS-Mediated Apoptosis

Figure 3:
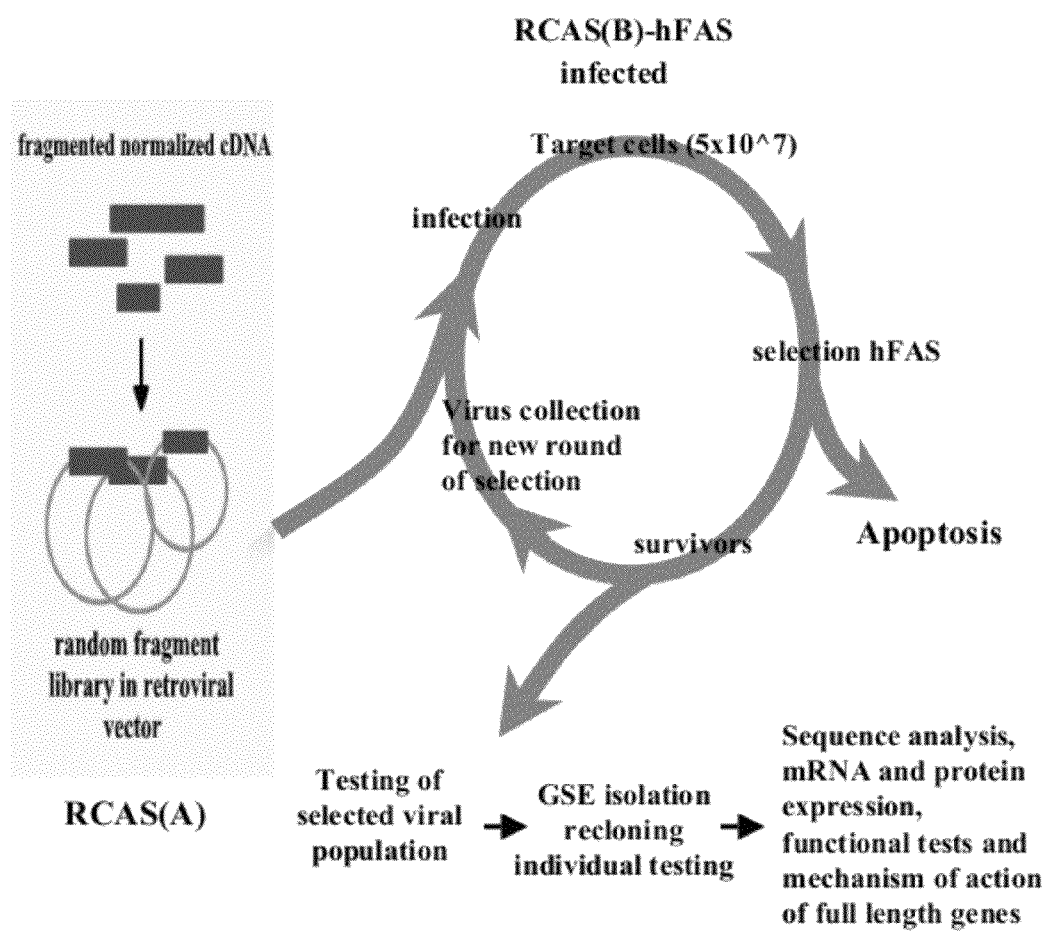
FIG. 3 shows a scheme of the RCAS system used to identify peptide fragment inhibitors of FAS apoptosis.
Figure 4:
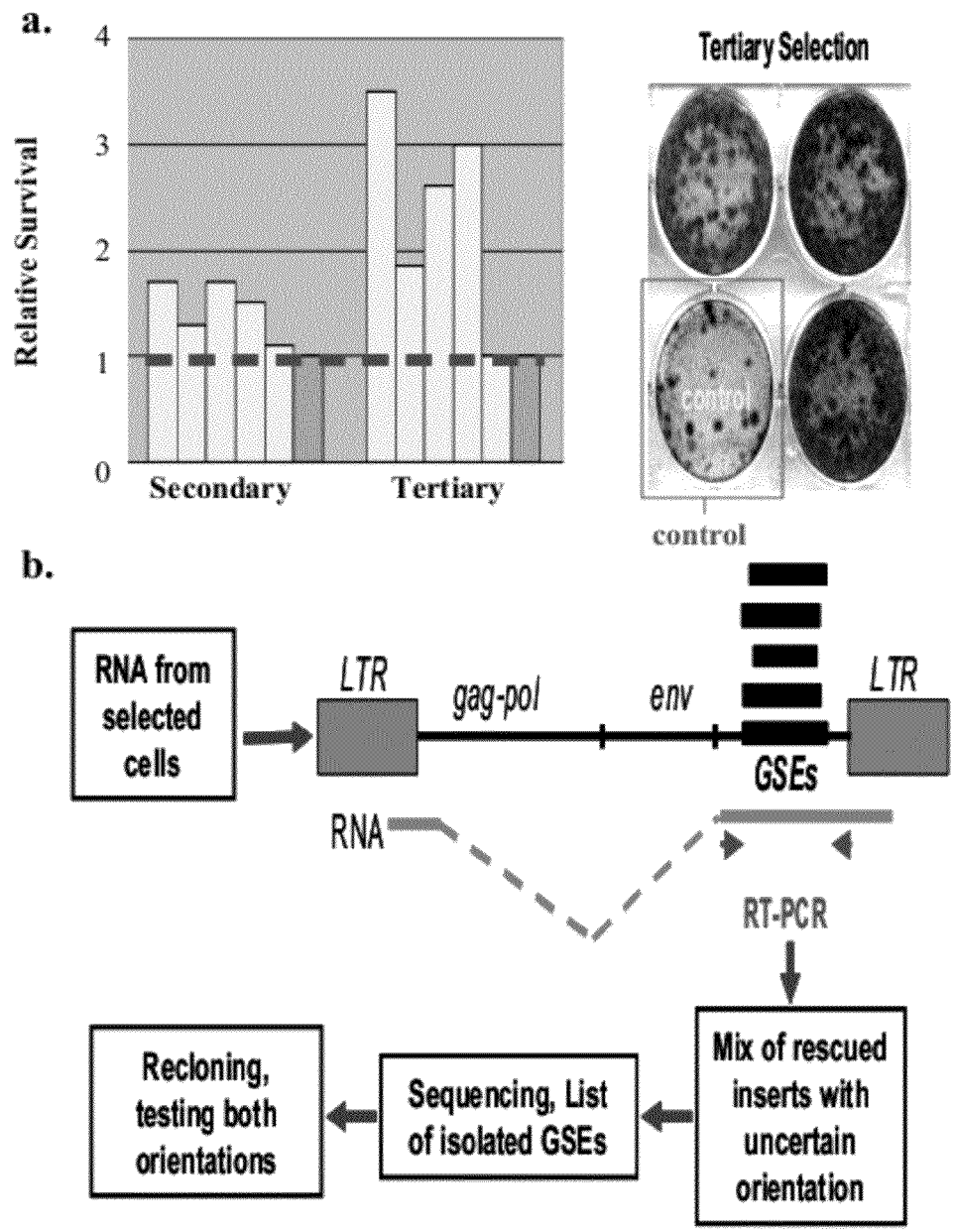
FIG. 4 shows a scheme for selection of peptide fragment inhibitors against FAS apoptosis. (a) 50 million cells were used for infection with the peptide fragment library and primary selection. Comparison of quantitation of methylene blue staining of survived colonies 7 days after FAS treatment in secondary and tertiary screening is shown. The bar graph represents relative survival of cells after selection as determined by methylene blue staining. (b) After 3 selections, RNA was isolated from the surviving cells.

The following results indicate the identification of cytoplasmic cytochrome b as a component of FAS-mediated apoptosis. A genetic suppressor analysis was undertaken to identify dominantly acting peptides that inhibit FAS-dependent apoptosis. A library of random peptide fragments of multidomain proteins was made using the replication-competent avian retroviral vector RCASBP(A). The library was overexpressed in human FAS receptor expressing cells. See FIG. 3. The cells were subjected to FAS apoptosis by treatment with a FAS agonistic antibody. The replication competency of RCAS vector allowed for several rounds of selection and screening by efficient rescue of viral particles. Virus particles from cells that did not undergo apoptosis carried RCASBP (A), which encoded peptide fragments (inserts) that inactivate FAS-dependent apoptosis. See FIG. 4. Fragments that inhibit apoptosis were then further characterized.

Total RNA from 5 individual selected populations of cells after the third round of selection was subjected to RT-PCR. A mix of FAS-dependent apoptosis inhibiters were sequenced and recloned individually back into the original vector RCASBP(A) in both sense and anti-sense orientation for determining whether sense or anti-sense of the candidate genetic suppressor elements orientation mediates the functional effect.

Overall there were 40 RCASBP(A) inserts sequenced. Four inserts were derived from the subunits of the mitochondrial electron-transport chain. GSE F21 corresponded to the cytochrome b subunit of complex III. Three GSEs (GSE F37, F2 and F26) were derived from the different subunits of complex IV, or cytochrome oxidase (Flock and Helms, 2002; Roberts and Pique, 1999). These complexes reside in the inner mitochondrial membrane. The normal function of Complex III is to donate the electrons to cytochrome c (Zhang et al., 1998), which then carries them to its electron acceptor—Complex IV (Flock and Helms, 2002; Yoshikawa et al., 1998).

Figure 5:
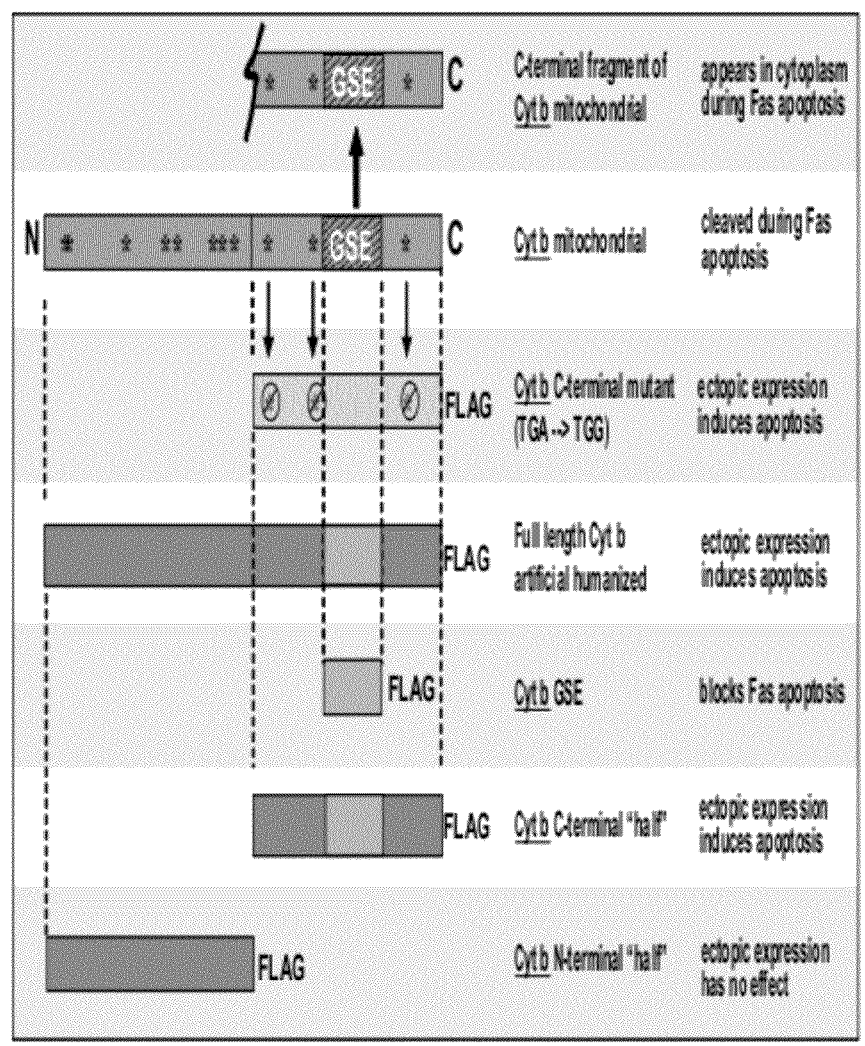
FIG. 5 shows a Scheme of generated Cyt b constructs and their activity.
Figure 6:
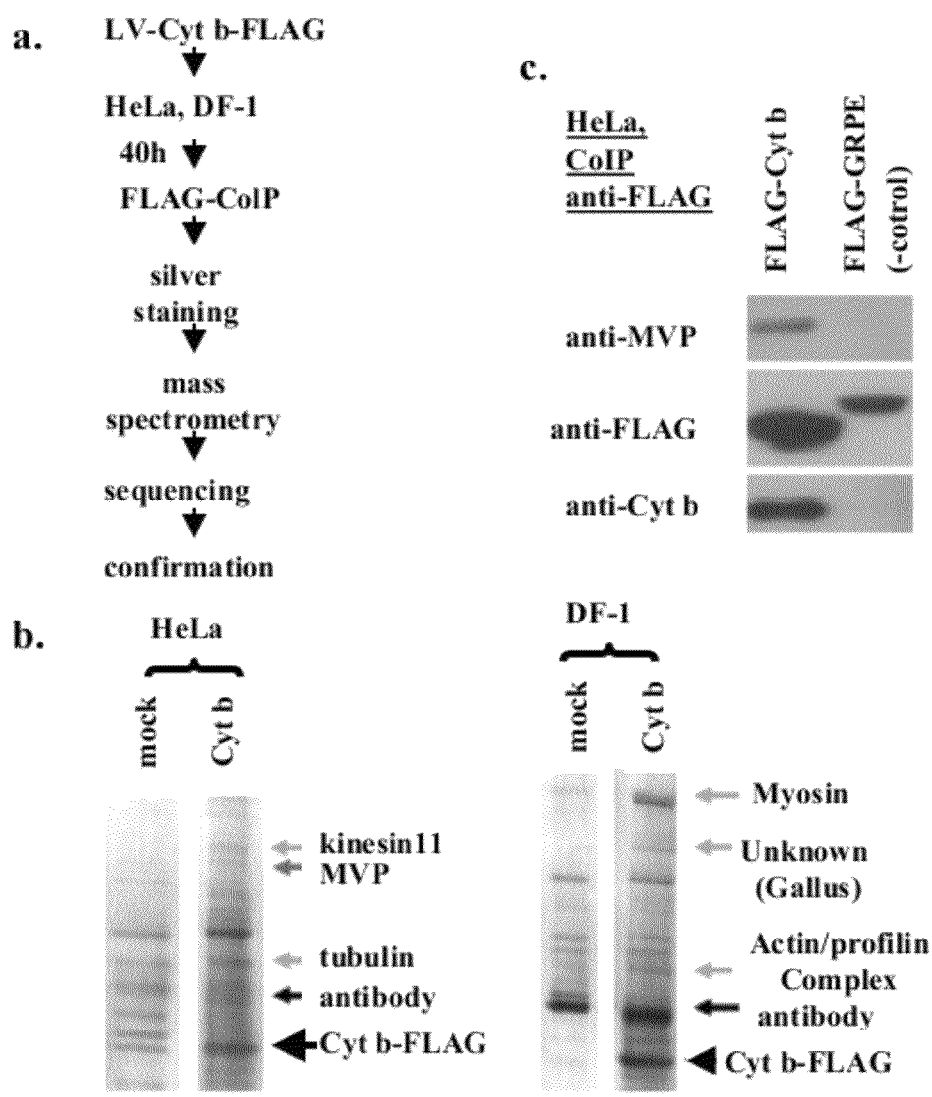
FIG. 6 shows the isolation of the modulators of cytochrome b of the FAS-mediated apoptosis system.

Although the peptides encoded by the inserts are expected to act against the genes of their origin, one could not exclude other mechanisms of their activity. It was therefore important to test whether cytb-insert could block apoptosis triggered by the expression of full-length Cyt b in the cytoplasm. To address this question, HeLa cells were transfected with cytochrome c-expressing vector combined with the insert-expressing construct at 1:1 ratio or with DNA of insert-free vector. Cytb-insert was originally isolated for its protective effect against FAS apoptosis, this result provides an important argument for Cyt b being a key mediator of FAS-induced apoptosis. See FIG. 5.

The cytotoxicity of Cyt b overexpression might reflect the natural process of pro-apoptotic release of Cyt b into cytoplasm. If Cyt b is involved in the downstream events of FAS signaling, then the mechanism of insert-mediated suppression of FAS may involve blocking the pro-apoptotic activity of the released Cyt b in the cytoplasm. Blocking of Cyt b apoptosis by GSE would recapitulate the effect of GSE against FAS apoptosis. From the results of coexpression of full-length Cyt b and its GSE in cytoplasm of Hela cells, GSE indeed blocks pro-apoptotic effect of Cyt b.

Accordingly, mitochondrial Cyt b is cleaved during FAS apoptosis, and its C-terminal part is released into cytoplasm. See FIG. 5. Since Cyt b is transcribed in the mitochondria, due to the differences in the nuclear and mitochondrial code, stop codons arise in sequences of mitochondrial genes when the gene is read in the nuclear code. An entirely artificial construct encoding the humanized cytochrome b sequence for cytoplasmic expression was generated. See FIG. 5. It was also supplied with FLAG sequence at the C-terminal and cloned into lentiviral expression vector under the CMV promoter. In addition to the full-length Cyt b, three other constructs were generated using the artificial copy of the gene as a template. C-terminal portion roughly corresponding to the released portion of Cyt b cDNA was now derived from the artificial sequence completed with humanized codons. GSE sequence was also generated separately from the same template. N-terminal portion of Cyt b was generated in a similar manner. See FIG. 5. All these constructs were supplied with C-terminal FLAG sequence. Infection of HeLa cells with the indicated constructs revealed that both full-length Cyt b and its C-terminal portion induce apoptosis, N-terminal portion has no effect, and the Cyt b insert protects the cells from apoptosis induced by cytoplasmic overexpression of Cyt b. Accordingly the above described results show that the Cyt b-insert is an effective blocker of FAS, and cytoplasmic Cyt b-induced apoptosis and Cyt b is released in response to FAS treatment from mitochondria. Therefore cytoplasmic Cyt b is an important component of the FAS-mediated apoptosis system.

Example 2

MVP Binds to Cytochrome b

The following results identify major vault protein as a counterpart of Cyt b. The following procedure was used to identify MVP as a regulator of Cyt b. FLAG-tagged Cyt b with FLAG at its C terminus was transduced by lentiviral infection into HeLa and DF-1 cells. Since cytoplasmic Cyt b was found to be toxic for these cells, cell lysates were collected 40 hours after infection when the majority of cells remained viable but apoptosis was already initiated, suggesting that newly synthesized Cyt b has reached its cytoplasmic targets. Cell lysates containing FLAG-tagged Cyt b, as well as the control mock-transduced cells lacking FLAG-tagged proteins, were collected and incubated with M2 anti-FLAG antibodies conjugated with agarose beads as described in U.S. Prov. Appl. No. 60/805,849. Cytoplasmic proteins coprecipitating with Cyt b-FLAG were loaded on two parallel PAA gels, one for silver staining, and the other for Western blot analysis with anti-FLAG and anti-Cyt b antibodies. The steps of identifying MVP as a regulator are shown schematically in FIG. 5a.

Both Western Blot Analysis and silver staining detected a strong band of approximately 30 kDa in the co-precipitates derived from cells overexpressing Cyt b as shown in FIG. 5b. This band was not present in the control. Along with several minor proteins in the experimental and control lanes, silver staining also yielded a major band of ectopically expressed Cyt b coinciding with the one detected by Western blot. A presumption was made that the proteins present in Cyt b coprecipitates, but absent in mock coprecipitation, interacted in a complex with Cyt b. All "suspicious" bands of the minor proteins were excised from the gel and given to Midwest Bio Services, Overland Park, Kans. Protein identification was performed according to the standard Midwest Bio Services protocol, as described in U.S. Prov. Appl. No. 60/805,849. Peptide sequences from the excised gels were generated by first performing a proteolytic digestion of the excised peptides bands, and then concentrating them onto a peptide trap column. The peptides were then separated on a reverse-phase chromatography column. MS and MS/MS spectra were acquired by the ion trap mass spectrometer. The sequences of the peptides were inferred by matching the mass sprectrometry spectra to protein sequence databases by the TURBOSE-QUEST software.

Overall, 10 proteins were identified as coprecipitating with Cyt b. Among them were cytoskeletal proteins of actin/profiling complex, myosin and tubule, as well as cytoskeleton-associated motor protein kinesis 11. Major Vault Protein (MVP) was also detected in the co-precipitate from HeLa cells. Both actin and kinesin were previously shown to be stable constituents of the vault complex, and may have been a consequence of their tight association with vault complex. Investigation of MVP as the functional mediator of Cyt b effects was confirmed by coimmunoprecipitation as shown in FIG. 5c. As for the identification of the Cyt b protein complex, FLAG-tagged Cyt b and FLAG-tagged GRPE (used as a negative control in this experiment) were transduced by lentiviral infection into HeLa cells, and cells were lysed at 40 hours after infection. Cell lysates containing Cyt b-FLAG, as well as the control GRPE-FLAG-transduced cells, were incubated with M2 anti-FLAG antibodies conjugated with agarose beads as described in U.S. Patent Prov. Appl. No. 60/805,849. Cytoplasmic proteins coprecipitating with FLAG-tagged constructs were loaded on PAA gel for Western blot analysis with anti-FLAG, anti-Cyt b and anti-MVP antibodies. Anti-FLAG antibodies detected both Cyt b and GRPE in the lysates prepared from the correspondingly transduced cells, whereas anti-Cyt b antibody detected Cyt b only in cells infected with Cyt b-FLAG. Anti-MVP antibodies detected a band of approximately 130 kDa, coinsiding with the expected molecular weight of MVP, in the coprecipitates derived from cells overexpressing FLAG-Cyt b but not in the lysates expressing FLAG-GRPE. Accordingly, the results indicate that MVP associates with Cytochrome b in cytoplasm.

Example 3

MVP Regulates FAS Mediated Apoptosis Through Cytochrome b

Figure 7:
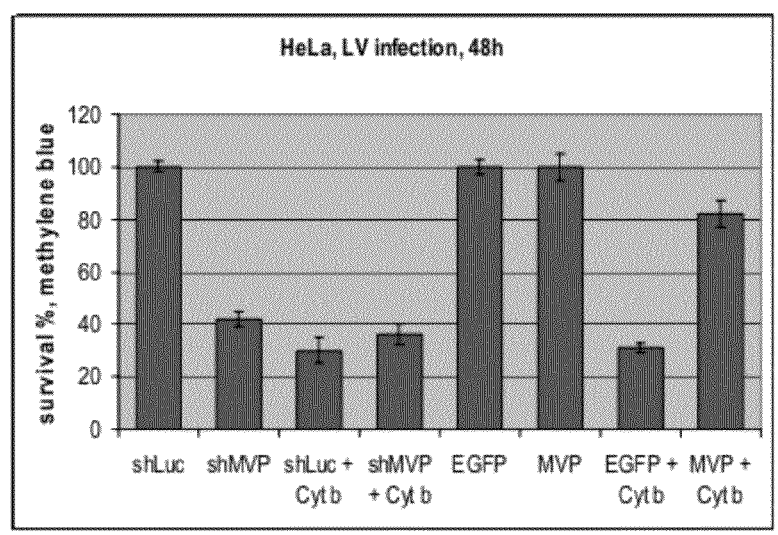
FIG. 7 shows that MVP regulates FAS-mediated apoptosis through modulation of cytoplasmic cytochrome b.
Figure 7:
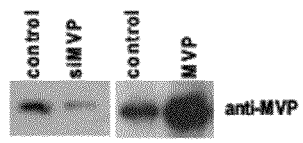
Figure 7:
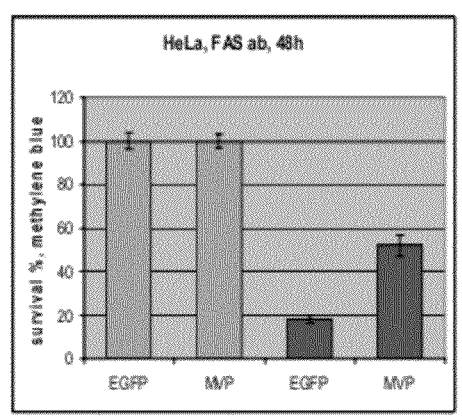

The following results indicate that MVP interacts with cytochrome b and suppresses fas-mediated apoptosis. A number of constructs were generated, including a construct that overexpresses MVP alone, MVP+cyto b, and a shMVP sequence+cyto b. These vectors were transfected into Hela cells via lentiviruses and the cells were subjected to Fas-apoptosis analysis. Fas ligand was added and the number of surviving Hela cells were counted after 48 hrs. post ligand addition. EGFP served as a negative control. In FIG. 7a it is shown that Hela cells expressing only MVP survive at a 100% rate. Cells with cyto b and EGFP survived at only a rate of 30%. Cells overexpressing MVP and cyto b indicate an 82% survival. These results indicate (1) MVP has a negative effect on cyto b and its role in FAS-mediated apoptosis. In FIG. 7c, cells not induced by FAS antibody, show 100% survival in cells that overexpress either EGFP or MVP. When FAS antibody is added to thees cells, results indicate that MVP provides a 2-fold increase in sruvival over EGFP negative control, accordingly these results indicate that MVP plays a direct role in fas-mediated apoptosis. Together these results indicate that MVP directly interactss with cytochrome b of the FAS-mediated apoptosis system.

The invention claimed is:

1. A method for screening a modulator of major vault protein comprising:
 (a) providing a cell comprising major vault protein and a FAS-mediated apoptosis system, wherein the FAS-mediated apoptosis system comprises a FAS receptor and cytochrome b;
 (b) providing a FAS ligand to the cell;
 (c) contacting the cell with a candidate modulator compound;
 (d) measuring the level of apoptosis of the cell; and
 (e) comparing the level of apoptosis of the cell to a control; wherein a modulator of major vault protein is identified by a change in apoptosis compared to the control.

2. The method of claim 1, further comprising selecting the candidate modulator from a library of compounds.

3. The method of claim 2, wherein the library of compounds is selected from the group consisting of a random peptide library, a natural products library, a cDNA library, a combinatorial library, an oligosaccharide library and a phage display library.

4. The method of claim 1, further comprising the step of overexpressing the major vault protein.

5. The method of claim 1, further comprising the step of expressing the major vault protein from heterologous DNA.

6. The method of claim 1, further comprising the step of expressing the FAS-mediated apoptosis system from heterologous DNA.

7. The method of claim 6, wherein the step of expressing the FAS-mediated apoptosis system comprises expressing the FAS receptor from a vector.

8. The method of claim 1, further comprising the step of expressing the cytochrome b from a vector.

9. The method of claim 1, wherein the method is performed in vitro.

10. The method of claim 1, wherein the method is high throughput.

11. The method of claim 1, wherein the FAS receptor ligand is selected from the group consisting of FAS receptor antibodies, FAS-L, FAS receptor specific ligands, and non-specific FAS receptor ligands.

12. The method of claim 1, wherein the cell is non-mammalian.

13. The method of claim 1, wherein the cell is mammalian.

14. The method of claim 13, wherein the mammalian cell is selected from the group consisting of CHO cells and HeLa cells.

15. A method for screening a modulator of FAS-mediated apoptosis, comprising identifying a modulator of major vault protein according to the method of claim 1, wherein a modulator of FAS-mediated apoptosis is identified as a modulator of major vault protein.

* * * * *